(12) United States Patent
DeAscanis et al.

(10) Patent No.: US 9,948,835 B2
(45) Date of Patent: Apr. 17, 2018

(54) SINGLE-AXIS INSPECTION SCOPE WITH SPHERICAL CAMERA AND METHOD FOR INTERNAL INSPECTION OF POWER GENERATION MACHINERY

(71) Applicant: Siemens Energy, Inc., Orlando, FL (US)

(72) Inventors: Joshua DeAscanis, Oviedo, FL (US); David Letter, Deland, FL (US); Isaac Piersall, Winter Springs, FL (US); Clifford Hatcher, Jr., Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 122 days.

(21) Appl. No.: 15/212,370

(22) Filed: Jul. 18, 2016

(65) Prior Publication Data
US 2016/0330351 A1    Nov. 10, 2016

Related U.S. Application Data

(63) Continuation-in-part of application No. 14/803,149, filed on Jul. 20, 2015, now Pat. No. 9,778,141, which
(Continued)

(51) Int. Cl.
*G01M 15/14* (2006.01)
*H04N 5/225* (2006.01)
(Continued)

(52) U.S. Cl.
CPC ......... *H04N 5/2251* (2013.01); *F01D 21/003* (2013.01); *G01M 15/02* (2013.01);
(Continued)

(58) Field of Classification Search
USPC .......................... 73/112.01, 112.02, 112.05
See application file for complete search history.

(56) References Cited

U.S. PATENT DOCUMENTS 4,216,802 A    8/1980   Bonnes et al.
5,102,221 A    4/1992   Desgranges et al.
(Continued)

FOREIGN PATENT DOCUMENTS

EP    0907077    4/1999

OTHER PUBLICATIONS

Utility U.S. Appl. No. 13/971,938, filed Aug. 21, 2013, now U.S. Pat. No. 9,154,743 issued on Oct. 6, 2015.
(Continued)

*Primary Examiner* — Eric S McCall (57) ABSTRACT

Internal components of power generation machinery, such as gas turbine engines, are inspected with a spherical optical camera inspection system mounted on a compact diameter, single-axis inspection scope that is capable of insertion within an inspection port or other accessible insertion site. The inspection scope includes nested, non-rotatable telescoping tubes, which define an extension axis. Circumscribing, telescoping tubes have anti-rotation collars, which are in sliding engagement with a mating axial groove on an outer circumferential surface of a circumscribed tube. The camera is advanced and/or retracted along a scope extension axis by nested, drive tubes, which incorporate at least one external drive screw on a circumscribed drive tube and corresponding female threads formed in a circumscribing drive tube. The spherical camera has a 360-degree field of view, and captures images without rotation about the scope extension axis.

20 Claims, 6 Drawing Sheets

Related U.S. Application Data is a continuation-in-part of application No. 13/362,352, filed on Jan. 31, 2012, now Pat. No. 8,713,999.

(51) Int. Cl.

| | | |
|---|---|---|
| *H04N 5/232* | (2006.01) | |
| *F01D 21/00* | (2006.01) | |
| *G01M 15/02* | (2006.01) | |
| *G02B 23/24* | (2006.01) | |
| *G01N 21/954* | (2006.01) | |
| *G06T 7/00* | (2017.01) | |
| *G02B 13/06* | (2006.01) | |

(52) U.S. Cl.
CPC .......... *G01M 15/14* (2013.01); *G01N 21/954* (2013.01); *G02B 13/06* (2013.01); *G02B 23/2484* (2013.01); *G06T 7/97* (2017.01); *H04N 5/2257* (2013.01); *H04N 5/23238* (2013.01); *F05D 2220/32* (2013.01); *F05D 2260/83* (2013.01); *F05D 2270/80* (2013.01); *G01N 2021/9544* (2013.01); *G06T 2207/20221* (2013.01); *H04N 2005/2255* (2013.01)

(56) References Cited

U.S. PATENT DOCUMENTS

| | | |
|---|---|---|
| 5,164,826 A | 11/1992 | Dailey |
| 5,349,850 A | 9/1994 | Young |
| 6,317,387 B1 | 11/2001 | D'Amaddio et al. |
| 6,992,315 B2 | 1/2006 | Twerdochlib |
| 7,068,029 B2 | 6/2006 | Hatcher et al. |
| 7,271,894 B2 | 9/2007 | Devitt et al. |
| 7,489,811 B2 | 2/2009 | Brummel et al. |
| 7,956,326 B1 | 6/2011 | Kychakoff et al. |
| 8,184,151 B2 | 5/2012 | Zombo et al. |
| 8,299,785 B2 | 10/2012 | Bousquet et al. |
| 8,713,999 B2 | 5/2014 | Hatcher |
| 8,922,640 B2 | 12/2014 | Hatcher et al. |
| 2004/0051525 A1 | 3/2004 | Hatcher et al. |
| 2004/0193016 A1 | 9/2004 | Root et al. |
| 2005/0073673 A1* | 4/2005 | Devitt .................. F01D 21/003 356/37 |
| 2005/0199832 A1 | 9/2005 | Twerdochlib |
| 2005/0200355 A1 | 9/2005 | Hatcher et al. |
| 2005/0288551 A1* | 12/2005 | Callister ............ A61B 1/00082 600/115 |
| 2006/0088793 A1 | 4/2006 | Brummel et al. |
| 2007/0038052 A1* | 2/2007 | Swoyer ................ A61N 1/0551 600/345 |
| 2007/0129604 A1 | 7/2007 | Hatcher et al. |
| 2007/0157733 A1 | 7/2007 | Litzenberg et al. |
| 2007/0296964 A1 | 12/2007 | Nishimura et al. |
| 2009/0312783 A1* | 12/2009 | Whayne ......... A61B 17/320016 606/190 |
| 2010/0305715 A1* | 12/2010 | Mathis ................ A61B 1/2676 623/23.65 |
| 2011/0004157 A1* | 1/2011 | Dewaele ............ A61B 1/00071 604/95.01 |
| 2011/0018530 A1 | 1/2011 | Bousquet et al. |
| 2011/0267428 A1 | 11/2011 | George et al. |
| 2012/0154594 A1 | 6/2012 | Xie et al. |
| 2012/0281084 A1 | 11/2012 | Hatcher et al. |
| 2013/0194412 A1 | 8/2013 | Hatcher et al. |
| 2013/0194413 A1 | 8/2013 | Hatcher et al. |
| 2014/0168420 A1 | 6/2014 | Naderhirn |
| 2014/0259641 A1* | 9/2014 | Brannan ............ A61B 18/1815 29/602.1 |
| 2014/0276739 A1* | 9/2014 | Brannan ............ A61B 18/1815 606/33 |
| 2015/0199805 A1* | 7/2015 | Hatcher, Jr. ............. G06T 7/004 348/135 |
| 2016/0010496 A1* | 1/2016 | Hatcher, Jr. ............. F01D 21/06 415/13 |
| 2016/0212360 A1* | 7/2016 | Williams ................ H04N 5/33 |

OTHER PUBLICATIONS

Utility U.S. Appl. No. 13/362,417, filed Jan. 31, 2012, now U.S. Pat. No. 9,057,710 issued on Jun. 16, 2015.
Utility U.S. Appl. No. 13/362,352, filed Jan. 31, 2012, now U.S. Pat. No. 8,713,999 issued on May 6, 2014.
Utility U.S. Appl. No. 13/362,387, filed Jan. 31, 2012, now U.S. Pat. No. 8,922,640 issued on Dec. 30, 2014.
Utility U.S. Appl. No. 13/972,000, filed Aug. 21, 2013, now U.S. Pat. No. 9,116,071 issued on Aug. 25, 2015.
Co-pending Utility U.S. Appl. No. 14/732,982, filed Jun. 8, 2015.
Co-pending Utility U.S. Appl. No. 14/803,149, filed Jul. 20, 2015.

\* cited by examiner

SINGLE-AXIS INSPECTION SCOPE WITH SPHERICAL CAMERA AND METHOD FOR INTERNAL INSPECTION OF POWER GENERATION MACHINERY

PRIORITY CLAIM

This application claims priority under, and is a continuation-in-part of U.S. utility patent application Ser. No. 14/803,149, filed Jul. 20, 2015, and entitled "Optical Inspection Scope with Deformable, Self-Supporting Deployment Tether", which is a continuation-in-part of U.S. utility patent application Ser. No. 13/362,352, filed Jan. 31, 2012, and entitled "System and Method For Automated Optical Inspection of Industrial Gas Turbines and Other Power Generation Machinery with Multi-Axis Inspection Scope", now U.S. Pat. No. 8,713,999, issued May 6, 2014, and claims priority to U.S. provisional patent application Ser. No. 61/692,393, filed Aug. 23, 2012, and entitled "Hybrid Scope—Turbine Combustor Hardware Visual Inspection Tooling That Can Also Be Used To Inspect The Row 1 Turbine Blades While They Are On Turning Gear (1-1000 rpm)", and claims priority to U.S. provisional patent application Ser. No. 61/692,409, filed Aug. 23, 2012, and entitled "Vision Scope—3D Scanner Tip for Visual Inspection and Measurement", the entire contents of each of which are incorporated by reference herein.

TECHNICAL FIELD

The invention relates to non-destructive, visual inspection of power generation machinery, such as gas turbine engines. More particularly, the invention relates to visual inspection of power generation machinery, such as gas turbine engines with an inspection system, having a single-axis inspection scope and spherical camera. In many embodiments, the inspection scope, with camera, is inserted into an inspection port of the machine.

BACKGROUND

As described in U.S. Pat. No. 8,713,999, issued May 6, 2014, and entitled "System and Method For Automated Optical Inspection of Industrial Gas Turbines and Other Power Generation Machinery with Multi-Axis Inspection Scope", power generation machinery, such as generators, or steam or gas turbine engines, are often operated continuously with scheduled inspection and maintenance periods, at which time the machine is taken off line and shut down, for inspection and repair of any components identified during the inspection. Further description herein will focus on exemplary gas turbine engine inspection. Once cooled, the now static gas turbine engine is inspected with optical camera inspection systems. Inspection scope embodiments shown and described in U.S. Pat. No. 8,713,999 incorporate multi-axis inspection scopes, which facilitate selective orientation of an optical inspection camera field of view within the engine, through rotation and articulation of jointed scope segments. In some embodiments, described in U.S. Pat. No. 8,713,999, the inspection scope has a single translation axis, with the ability to rotate the camera field of view 360 degrees. Single translation axis, rotating field of view scope embodiments are described as useful for insertion between blade and vane rows in a turbine engine.

SUMMARY OF INVENTION

The present inventors recognized a need to develop an optical camera inspection system with a small diameter component envelope, for insertion into relatively small engine inspection ports of diameters as little as 1.709 inches (43.41 millimeters). Thus, with use of exemplary embodiments described herein, any ports, or other passages, greater than 43.41 millimeters is a potential scope insertion sites, such as combustor pilot nozzle passages.

Exemplary embodiments of the optical inspection scopes of the present invention are insertable into engine, or other power generation machinery, inspection ports, or other potential scope insertion sites, as small as 1.709 inches (43.41 millimeters). Internal components of the machine, such as a gas turbine engine, are inspected with a spherical optical camera inspection system mounted on a compact diameter, single-axis inspection scope. The scope, including the camera is capable of insertion within an inspection port or other accessible insertion site. The inspection scope includes nested, non-rotatable telescoping tubes, which define an extension axis. Circumscribing, telescoping tubes have anti-rotation collars, which are in sliding engagement with a mating axial groove on an outer circumferential surface of a circumscribed tube. In some embodiments, the mating anti-rotation collar incorporates one or more ball bearings, which engage the corresponding axial groove and in combination form a linear sliding bearing. The spherical camera has a 360-degree field of view, and captures internal images of the engine or other power generation machine, without rotation about the scope extension axis. The camera is advanced and/or retracted along a scope extension axis by nested, drive tubes, which incorporate at least one external drive screw on a circumscribed drive tube and corresponding female threads formed in a mating, circumscribing drive tube. In some embodiments, the camera field of view is advanced within the inspected machine, and images are captured at respective advancement positions. In some embodiments, an image processing system combines the respective images into a navigable composite image.

Exemplary embodiments of the invention feature a system for internal inspection of a power generation machine. The system comprises a single-axis, extendable inspection scope, for insertion into an inspection port of a power generation machine. The inspection scope has first, and second nested, telescoping tubes, respectively having proximal and distal ends and axial length. The second telescoping tube has an axial groove on an outer circumferential surface thereof. The first telescoping tube has a first anti-rotation collar coupled proximal the distal end thereof, in sliding engagement with the axial groove of the second telescoping tube. The scope also has first and second nested drive tubes retained within the telescoping tubes, respectively having proximal and distal ends and axial length. The first drive tube has a first drive bushing coupled to the distal end thereof, both of which are rotatable within the telescoping tubes, with the first drive bushing defining a bore with female drive threads. The second drive tube defines external male drive threads in engagement with the first drive bushing female threads. A camera-mounting collar is rigidly coupled to the respective distal ends of the second telescoping tube and the second drive tube, which prevents relative rotation thereof. A rotatable drive hub is coupled to the proximal end of the first drive tube, for selective rotation thereof. A mounting flange is coupled to the first telescoping tube, for affixation to an inspection port of a power generation machine. The system also includes a spherical camera, having a 360-degree field of view, coupled to the camera-mounting collar, for insertion into a power generation machine and capture of inspection images therein.

In some embodiments, a distal portion of the rotatable drive hub is oriented within the proximal end of the first telescoping tube, and engaged within the first drive tube, while a proximal portion of the drive hub is coupled to a driven gear that is external the first telescoping tube. In this particular embodiment, a first drive gear is engaged with the driven gear, for rotating the driven gear and the drive hub. A drive apparatus is coupled to the first drive gear, such as a hand crank or an electric motor. Some embodiments incorporate in parallel hand crank and electric motor drives, each coupled to its own drive gear. In some embodiments, one or more anti-rotation collars retain a ball bearing that is in engagement with a corresponding axial groove formed within the outer circumference of a mating, circumscribed, telescoping tube, which in combination comprise a linear bearing assembly. In some embodiments, the camera is retained within a camera housing that is coupled to the camera-mounting collar. In some embodiments, the camera housing also includes an illumination system, such as an array of light emitting diodes ("LEDs"). In some embodiments, the system includes a position encoder, for correlating hub rotation with axial displacement of the camera field of view; and an image processing system coupled to the camera and the position encoder, for storing plural images taken at different camera axial displacement positions, and for combining plural inspection images into a composite image. The inspection scopes, in some embodiments, comprise more than two telescoping tubes and/or more than two nested drive tubes.

Other exemplary embodiments of the invention feature a system for internal inspection of a power generation machine. The system comprises a single-axis, extendable inspection scope, which defines an extension axis, for insertion into an inspection port of a power generation machine. The scope has first, second, third, and fourth nested, telescoped tubes; respectively they have proximal and distal ends and axial length. The second, third and fourth telescoping tubes respectively have an axial groove on an outer circumferential surface thereof. The first telescoping tube has a first anti-rotation collar coupled proximal the distal end thereof, in sliding engagement with the axial groove of the second telescoping tube. The second telescoping tube has a second anti-rotation collar coupled proximal the distal end thereof, in sliding engagement with the axial groove of the third telescoping tube. The third telescoping tube has a third anti-rotation collar coupled proximal the distal end thereof, in sliding engagement with the axial groove of the fourth telescoping tube. The scope also has first, second, and third nested drive tubes retained within the telescoping tubes, respectively having proximal and distal ends and axial length. The first drive tube has a first drive bushing coupled to the distal end thereof, both of which are rotatable within the fourth telescoping tube. The first drive bushing defines a bore with female drive threads. The second drive tube defines external male threads in engagement with the first drive bushing female threads, and has a second drive bushing coupled to the distal end thereof, both of which are rotatable within the fourth telescoping tube. The second drive bushing defines a bore with female drive threads. The third drive tube defines external male threads in engagement with the second drive bushing female threads. The inspection system further includes a camera-mounting collar rigidly coupled to the respective distal ends of the fourth telescoping tube and the third drive tube, preventing relative rotation thereof. A rotatable drive hub is coupled to the proximal end of the first drive tube, for selective rotation thereof. A mounting flange is coupled to the first telescoping tube, for affixation to an inspection port of a power generation machine. The inspection system also includes a spherical camera, having a 360-degree field of view, coupled to the camera-mounting collar, for insertion into a power generation machine and capture of inspection images therein. In some embodiments, the system includes a position encoder, for correlating hub rotation with axial displacement of the camera field of view; and an image processing system coupled to the camera and the position encoder, for storing plural images taken at different camera axial displacement positions, and for combining plural inspection images into a navigable composite image.

Additional exemplary embodiments of the invention feature a method for internal inspection of a power generation machine. In practicing the method, a system for inspection of a power generation machine is provided. The system includes a single-axis, extendable inspection scope, which defines an extension axis, for insertion into an inspection port of a power generation machine. The provided scope has first, and second nested, telescoping tubes, respectively having proximal and distal ends and axial length. The second telescoping tube has an axial groove on an outer circumferential surface thereof. The first telescoping tube has a first anti-rotation collar coupled proximal the distal end thereof, in sliding engagement with the axial groove of the second telescoping tube. First and second nested drive tubes are retained within the telescoping tubes, respectively having proximal and distal ends and axial length. The first drive tube has a first drive bushing coupled to the distal end thereof, both of which are rotatable within the telescoping tubes. The first drive bushing defines a bore with female drive threads. The second drive tube defines external male drive threads in engagement with the first drive bushing female threads. The scope also has a camera-mounting collar rigidly coupled to the respective distal ends of the second telescoping tube and the second drive tube, preventing relative rotation thereof. A rotatable drive hub is coupled to the proximal end of the first drive tube, for selective rotation thereof. A mounting flange is coupled to the first telescoping tube, for affixation to an inspection port of a power generation machine. A spherical camera, having a 360-degree field of view, is coupled to the camera-mounting collar, for insertion into a power generation machine and capture of inspection images therein. In practicing the method, the provided inspection scope's mounting flange is affixed to an inspection port of a power generation machine, or other inspection entry site of the machine, while inserting the inspection scope therein. Thereafter the drive hub is rotated, thereby rotating the first drive tube, which in turn advances the second drive tube and the camera field of view within the power generation machine, without rotating the camera about the extension axis of the inspection scope. Respective camera images within the power generation machine are captured at plural positions, as the camera field of view is advanced within the machine.

Features of the exemplary embodiments of the invention described herein may be applied jointly or severally, in any combination or sub-combination.

BRIEF DESCRIPTION OF DRAWINGS

The exemplary embodiments of the invention can be understood by considering the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Exemplary embodiments of the invention are utilized for inspection of internal components of power generation machinery, such as gas turbine engines. The engine internal components are inspected with a spherical optical camera inspection system mounted on a compact diameter, single-axis inspection scope that is capable of insertion within an inspection port or other accessible insertion site. In some embodiments, the inspection scope, with camera, is inserted through a combustor pilot port, through the corresponding combustor transition and stopping before the row 1 vanes, with a view of the row 1 blades and vanes. The system is capable of capturing images along the camera translation path. Plural images are combined to generate a composite image of components within the inspection path. In some embodiments, the composite image is navigable, analogous to "street view" geographic path images available on some Internet-based map and trip navigation sites.

The inspection scope includes nested, non-rotatable telescoping tubes, which define an extension axis. Circumscribing, telescoping tubes have anti-rotation collars, which are in sliding engagement with a mating axial groove on an outer circumferential surface of a circumscribed tube, with the groove and collar forming a linear slide. The camera is advanced and/or retracted along a scope extension axis by nested, drive tubes, which incorporate at least one external drive screw on a circumscribed drive tube and corresponding female threads formed in a mating, circumscribing drive tube. In some embodiments, the female threads are formed in a drive bushing coupled to the corresponding drive tube. The spherical camera has a 360-degree field of view, and captures images without rotation about the scope extension axis.

Figure 1:
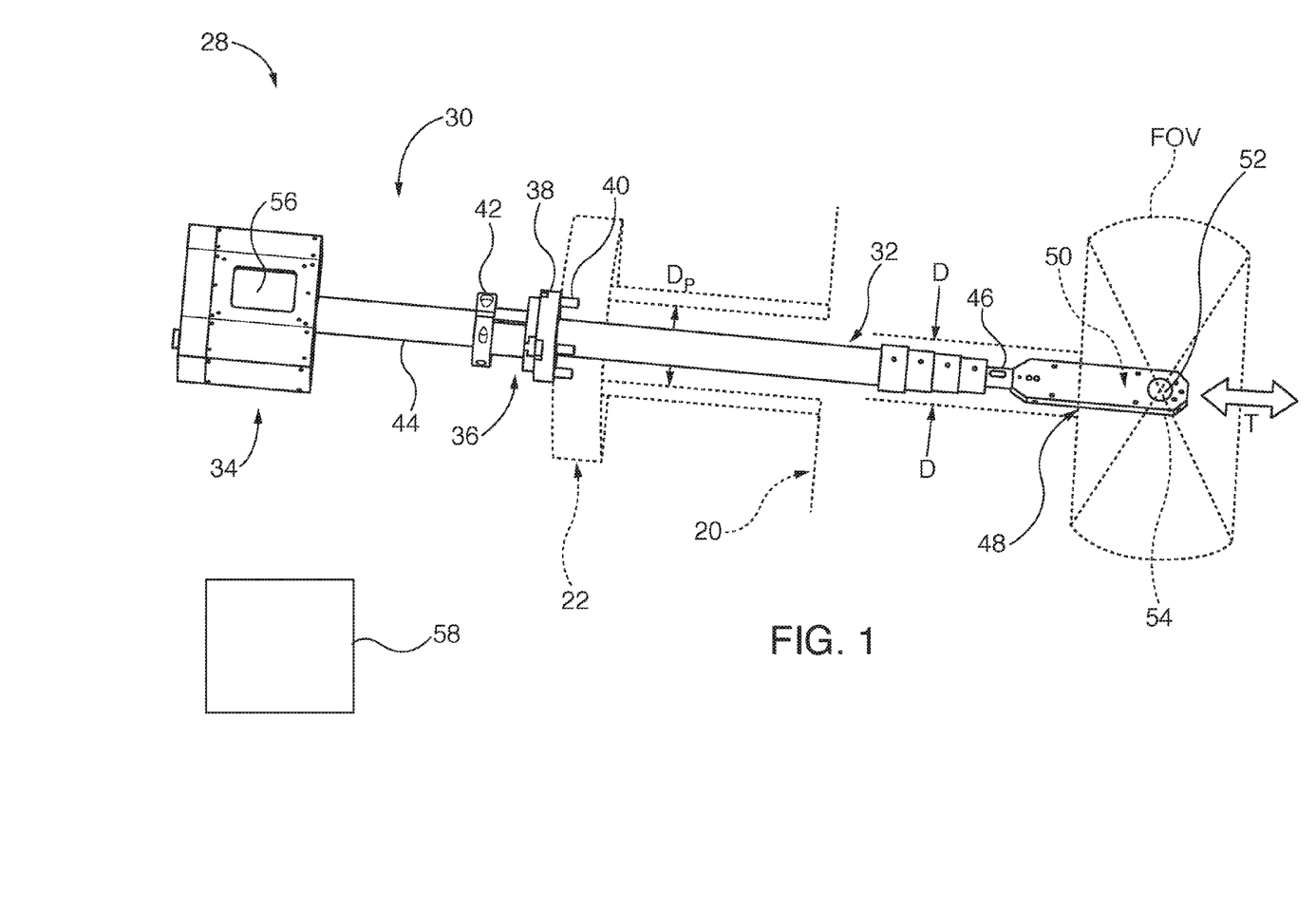
FIG. 1 is a top plan view of an embodiment of an inspection scope of the invention inserted within an inspection port of a power generation machine, such as an inspection port of a gas turbine engine.

FIG. 1 shows an exemplary power generation machine, such as a gas turbine engine 20, which includes an inspection port 22, with an internal passage minimum clearance diameter $D_p$. The term "port" as used herein includes dedicated inspection ports, which are sealed after completion of inspections, or any other type entry aperture that allows passage of an inspection scope into the engine interior. Other types of exemplary entry apertures or inspection access sites include a combustion pilot nozzle insertion aperture within a combustor, or a manway access cover of a gas turbine engine. The exemplary inspection system 28 includes an inspection scope 30, which has a telescoping portion 32 for insertion into the engine 20, a controller box 34 remains outside the engine. The inspection scope 30 includes a mounting collar 36 coupled to the telescoping portion 32, with a mounting flange 38 that is affixed to the inspection port 22 by fasteners 40. The mounting collar 36 includes a mounting collar-retaining clamp 42 that is clamped adjustably along an exterior surface of an outer or first telescoping tube 44. The retaining clamp 42 is selectively positioned and clamped axially relative to the first telescoping tube 44, as needed or desired for any particular inspection procedure. A camera-mounting collar 46 is coupled to a distal end of the inspection scope-telescoping portion 32, and is coupled to a camera housing 48. The camera housing 48 retains a spherical camera 50, which has a 360 degree field of view ("FOV"), for capturing images of components within the engine 20, without the need to rotate (pan) the camera FOV about an extension axis of the inspection scope telescoping portion 32. The spherical camera 50 has a first camera lens 52 on one side of the camera housing 48, and a second camera lens 54 on the other side of the camera housing, which in this particular embodiment is oriented 180 degrees opposite the first camera lens 52. The inspection scope 30 includes a visual display 56 retained within the controller box 34, for real-time monitoring of images being captured by the camera 50, or for retrieval of previously captured and stored images. Optionally, camera images are viewed remotely, and the inspection scope controlled remotely by an external computing device, such as a tablet computer 58. The tablet computer 58 communicates with the inspection scope 30 by hardwire cable (not shown) or by a wireless communication pathway. The inspection scope-telescoping portion 32 and the camera housing 48 have a maximum outside diameter D, which is smaller than the port minimum clearance diameter $D_p$. Working embodiments of the inspection scope have been constructed with a maximum outside diameter of 1.68 inches (42.67 millimeters) and a telescopic extension range of 48 inches (1220 millimeters) along an extension axis T.

Figures 2, 3, 4:
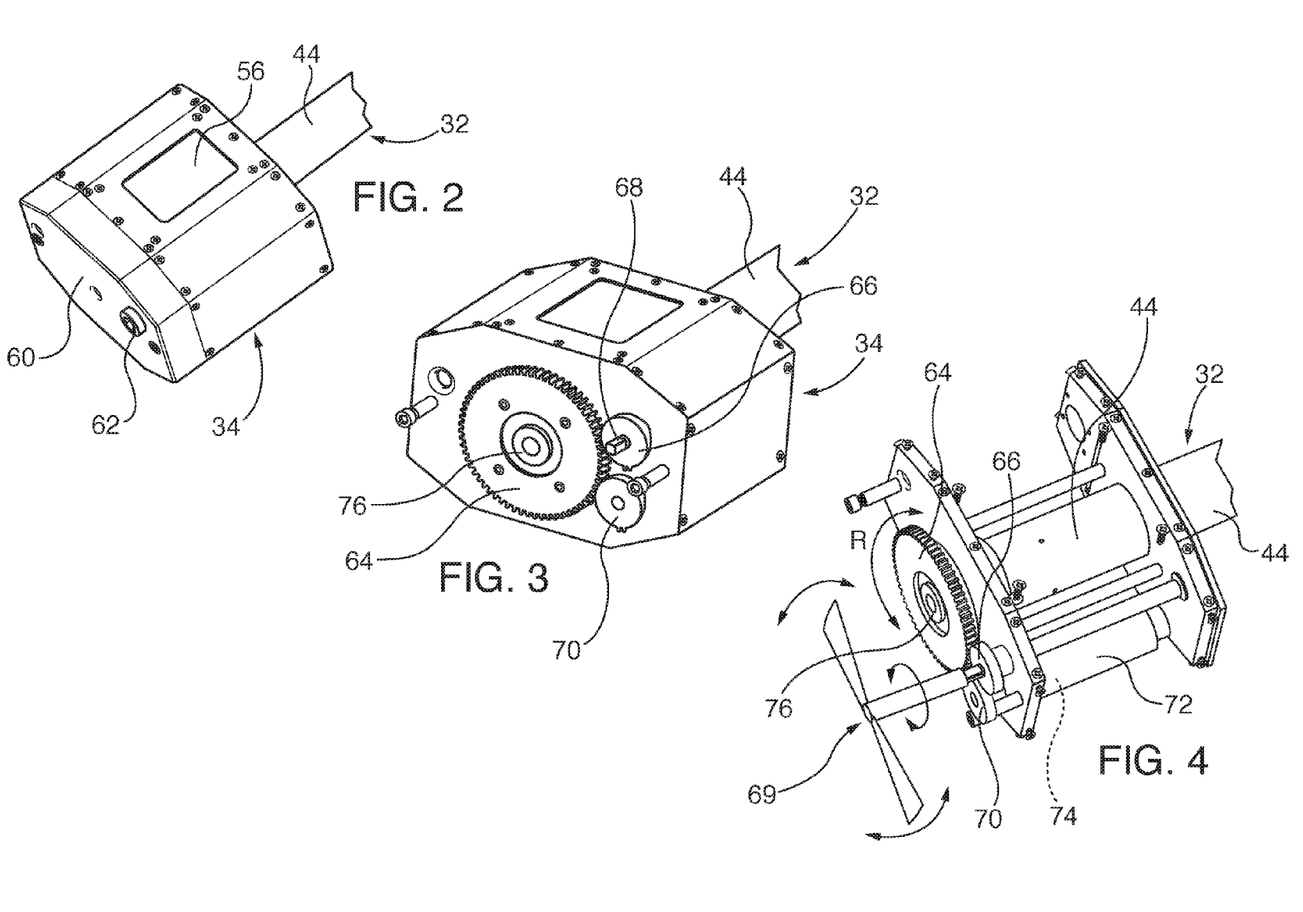
FIG. 2 is a top perspective view of a controller box of the inspection scope of FIG. 1.
FIG. 3 is an end perspective view of the controller box of FIG. 2, after removal of a gear cover, showing drive gears and a driven gear.
FIG. 4 is a top perspective view of the controller box of FIG. 2, after removal of outer covers, showing a motorized drive gear and a manually-cranked drive gear engaging the driven gear.
Figure 5:
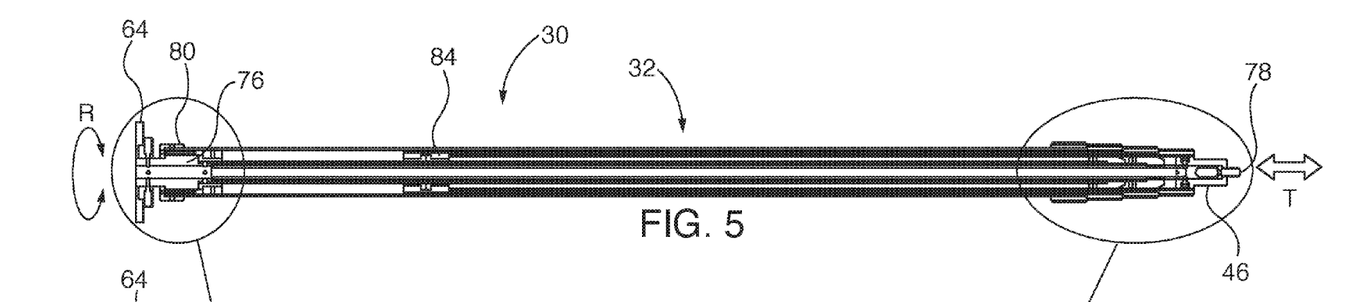
FIG. 5 is an axial cross-sectional view through telescoping tubes and drive tubes of the inspection scope of FIG. 1.

FIGS. 2-4 show the controller box 34, with a fragmentary view of proximal portions of the inspection scope-telescoping portion 32 and its first or outer telescoping tube 44. The controller box 34 has a removable gear cover 60, and an externally accessible hand crank socket 62, for selective coupling to a hand crank 69. Toothed driven gear 64 engages mating teeth of the first drive gear 66, which has a drive gear hub extension 68 that is coupled to the external hand crank socket 62. In FIG. 4, the hand crank 69 is shown directly coupled to the drive gear 64, without the gear cover 60 or the hand crank socket 62, to illustrate how the scope telescoping portion 32 is advanced or retracted along the telescoping extension axis/dimension T, by rotation of the drive gear 64. The inspection scope 30 also has a motorized drive for advancing and retracting the telescoping portion 32, which operates in parallel with and independently from the manual or hand-cranking drive. The toothed, second drive gear 70 engages mating teeth of the driven gear 64. Electric motor 72, which is a known motor used in motion control systems, drives the second drive gear 70. In this embodiment, the motor 72 incorporates a rotary positon encoder, which generates encoder data indicative of the number of motor shaft turns. The inspection scope 30 converts rotary motions R of the driven gear 64 into linear translation T of the telescoping portion 32. Thus, the rotary motion of the motor drive shaft and the position encoder data are correlated with linear translation of T of the telescoping portion 32. Other types of known position encoders can be substituted for the motor internal position encoder 74. The driven gear 64 is coupled to a rotatable drive hub 76, so that rotation of the drive gear 64 by either the first drive gear 66 or the second drive gear 70 also rotates the drive hub 76.

FIGS. 1 and 5-9 show internal construction of the inspection scope-telescoping portion 32. A proximal end of the telescoping portion 32 retains the driven gear 64 and the rotatable hub 76, while the camera-mounting collar 46 and camera housing mounting screw 78 are oriented on its distal end. The first or outer telescoping tube 44 retains a drive hub roller bearing 80 and a hub support bushing 82, for mounting of the rotatable hub 76, as well as a drive tube support bushing 84, for retention of a first or outer drive tube 86. The first drive tube is coupled to the rotatable hub 76 by first pin 88. Rotation of the driven gear 64 in the clockwise or counterclockwise directions R in turn rotates the hub 76 and the first drive tube 86. Interconnection of the first drive tube 86 to other downstream, distal second 112 and third 122 drive tubes, and their operation is described greater detail later herein.

The inspection scope-telescoping portion 32 comprises first or outer 44, second 92, third 96 and fourth 100 nested telescoping tubes, which in turn retain nested first or outer 86, second 112, and third or inner 122 drive tubes. Advancement or retraction of the drive tubes and telescoping tubes adjusts the axial length T of the inspection scope-telescoping portion 32. The telescoping tubes 44, 92, 96 and 100 incorporate anti-rotation structural features, which prevent rotation of the camera housing 48 about the extension axis of the telescoping portion 32. Each abutting pair of telescoping tubes incorporates one or more linear bearings, with the circumscribing telescoping tube including an anti-rotation collar and one or more retained ball bearings, which ride in a mating axial groove formed in the outer circumference of the circumscribed telescoping tube. The compact linear bearing construction facilitates relatively small maximum diameter D of the telescoping tubes and collars of 1.68 inches (42.67 millimeters). More particularly, the first telescoping tube 44 has a first anti-rotation collar 90, which engages a corresponding axial groove formed in the second telescoping tube 92. In turn, the second telescoping tube has a second anti-rotation collar 94, which engages an axial groove formed in the third telescoping tube 96. The third telescoping tube 96 in turn has a third anti-rotation collar 98, which engages an axial groove formed in the fourth or inner telescoping tube 100. A fourth tube collar 102 is rigidly coupled to the fourth telescoping tube 100, which is in turn rigidly couples that tube to the camera mounting collar 46. Screws 124 in turn rigidly couple the camera mounting collar 46 to the third or inner drive tube 122, so that the camera housing 48 does not rotate about the extension axis of the inspection scope's telescoping portion 32. Rigid affixation of the third drive tube 122 to the camera mounting collar 46 facilitates routing of cables between the camera housing 48 and the controller box 34, through the third drive tube's lumen 128 and apertures 128 formed in the camera mounting collar 46.

Figure 6:
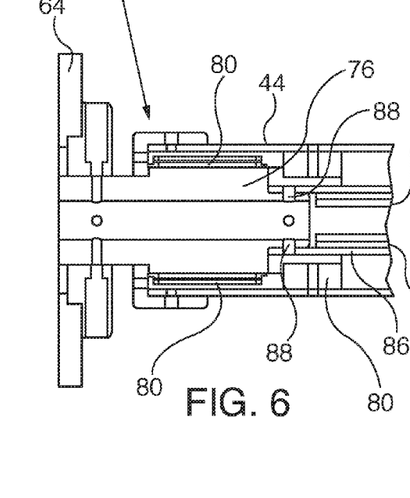
FIG. 6 is a detailed, fragmentary axial cross-sectional view through an outer telescoping tube and a rotatable drive hub at a proximal end of the inspection scope of FIG. 5.
Figure 7:
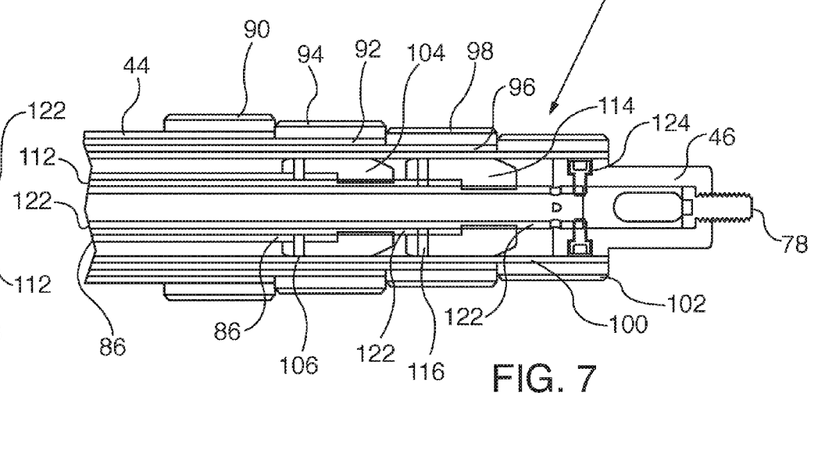
FIG. 7 is a detailed, fragmentary axial cross-sectional view through all of the telescoping tubes and drive tubes, at a distal end of the inspection scope of FIG. 5.
Figure 8:
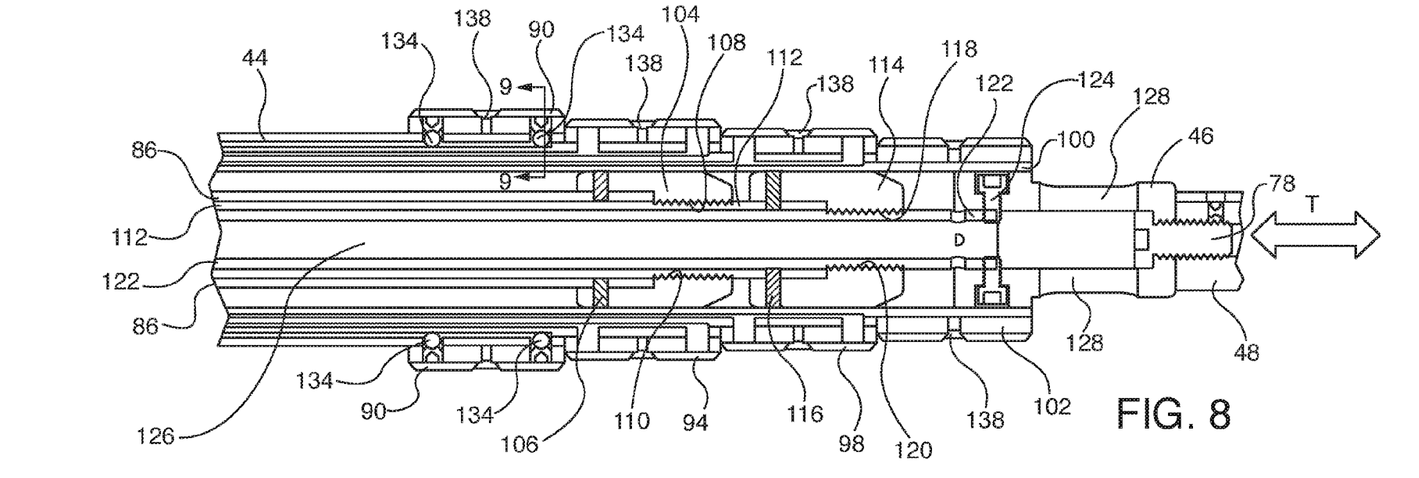
FIG. 8 is an elevational axial cross sectional view of the inspection scope of FIG. 7, oriented normal to the view of FIG. 7, and taken through an anti-rotation collar of a first or outer telescoping tube.

Structure and operation of the first 86, second 112 and third or inner 122 drive tubes is now described, with reference to FIGS. 6-8. As previously described, rotation of the rotatable hub 76 in either direction R rotates the first or outer drive tube 86, which are interconnected by the first pin 88. A first drive bushing 104 is rigidly coupled to a distal end of the first drive tube 86, by a first drive bushing-pin 106. The first drive bushing 104 and the first drive tube 86 are freely rotatable within the inner lumen of the fourth or inner telescoping tube 100. The first drive bushing 104 defines internal female drive threads (e.g., Acme profile drive threads) 108, which engage corresponding male external drive threads 110 formed on the outer circumference of the second drive tube 112. Rotation of the first drive tube 86 advances the external drive threads 110 relative to the rotating first drive bushing 104, thus advancing the second drive tube to the right in FIG. 8, along the extension axis T. A rotation stop is incorporated in the proximal end of the second drive tube 112, such as a pin or screw driven into a trough in the threads 110 profile, in order to prevent axial separation between the first 86 and second 112 drive tubes. When the second drive tube 112 proximal-end rotation stop contacts the first drive bushing 104, further rotation of the rotatable hub 76 also commences rotation of the second drive tube.

A distal end of the second drive tube 112 incorporates a rigidly mounted second drive bushing 114, which are rigidly connected to each other by second drive bushing-pin 116. The second drive bushing 114 defines female threads, which engage corresponding male external threads 118 on the outer circumference of the third or inner drive tube 122. The second drive bushing 114 and the second drive tube 112 are freely rotatable within the inner lumen of the fourth or inner telescoping tube 100. The second drive bushing 114 defines internal female drive threads (e.g., ACME profile drive threads) 108, which engage corresponding male external drive threads 120 formed on the outer circumference of the third drive tube 122. Rotation of the second drive tube 112 with first drive tube 86 advances the external drive threads 120 relative to the rotating second drive bushing 114, thus advancing the third drive tube 122 to the right in FIG. 8, along the extension axis T. A rotation stop is incorporated in the proximal end of the third drive tube 122, such as a pin or screw driven into a trough in the threads 120 profile, in order to prevent axial separation between the second 112 and third or inner 122 drive tubes. The inner drive tube 122 is rigidly coupled to the camera-mounting collar 46 and the fourth or inner telescoping tube 100. The inner drive tube cannot rotate relative to the extension axis T.

Figure 9:
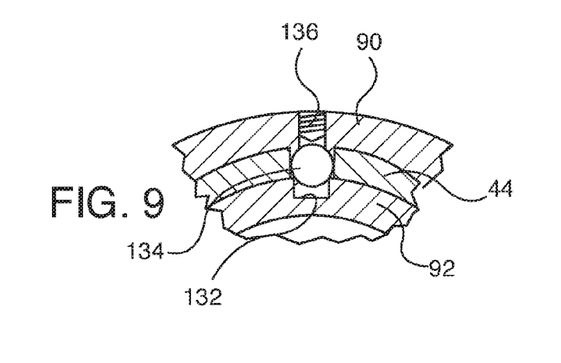
FIG. 9 is a cross-sectional view of an anti-rotation collar of the scope of FIG. 1, taken through 9-9 of FIG. 8.

FIGS. 8 and 9 show in detail the linear bearing structure that prevents relative rotation among the telescoping tubes 44, 92, 96 and 100. Focusing on the mating interface between the circumscribing first telescoping-tube 44 and its abutting, inscribed, second telescoping-tube 92, the latter has axial groove 132, which is parallel to the extension axis of the inspection scope. The axial groove 132 terminates inboard of the proximal and distal ends of the second telescoping tube 92, in order to prevent axial separation from the first telescoping tube 44. The first anti-rotation collar 90 retains ball bearings 134, which are in engagement with the axial groove 132. Respective ball bearing tensioning screws 136 selectively adjust the ball bearing 134 pressure against the mating axial groove 132. The respective second 94, and third 98 anti-rotation collars incorporate the same linear bearing construction, with mating axial groove in the circumscribed, inner mating tube (including axial separation prevention during tube extension) and ball bearing, as the first anti-rotation collar 90. All of the aforementioned anti-rotation collars are affixed to its corresponding telescoping tube by retention screws 138.

Figure 10:
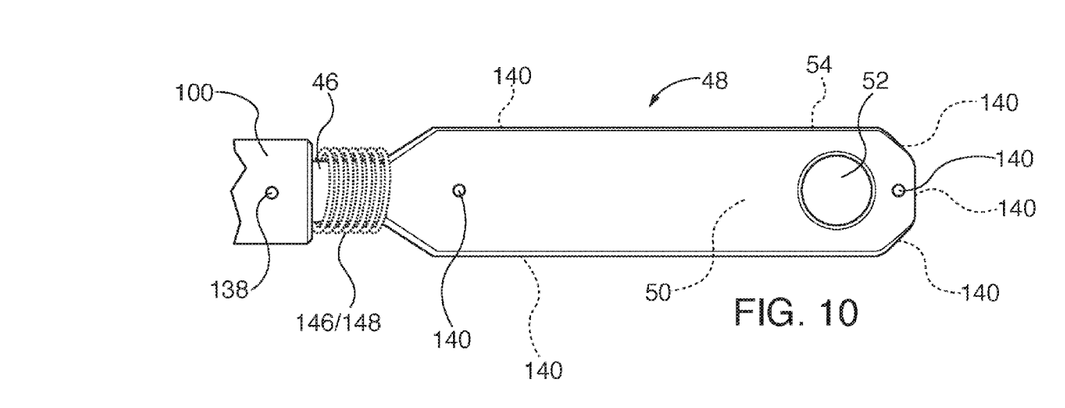
FIG. 10 is a top plan view of a camera housing of the scope of FIG. 1.
Figure 11:
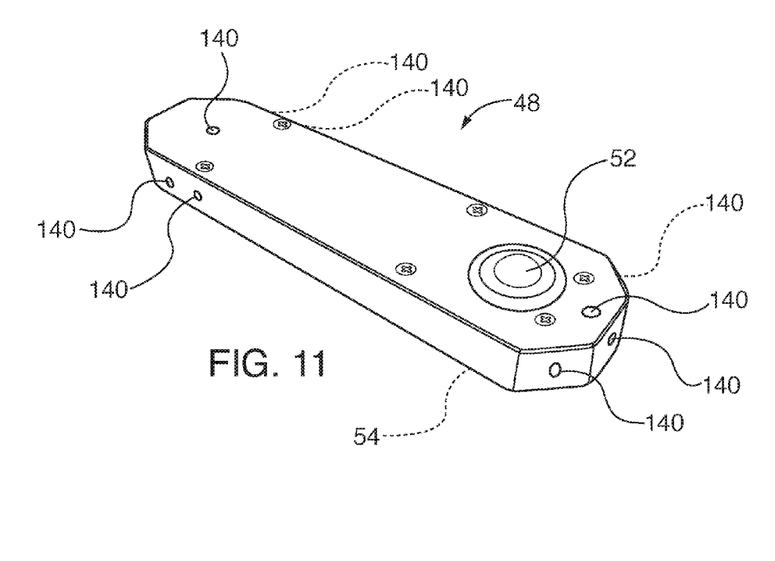
FIG. 11 is a perspective view of a camera head of FIG. 1.

FIGS. 8, 10, and 11 show further structural details of the camera housing 48. The camera housing 48 as coupled to the camera-mounting collar 46 by housing mounting screw 78. The housing 48 retains the spherical camera 50, and defines apertures for the camera lenses 52 and 54 on opposite sides of the housing. In this exemplary embodiment, the spherical camera 50, with 360-degree field of view, is an off-the-shelf, commercially available camera with corresponding operation software, such as a model Theta S camera, manufactured by Ricoh Company, Ltd. of Tokyo Japan, and sold by Ricoh USA, Inc. of Malvern Pa. USA. The camera housing 48 also provides apertures 140 for retention of illumination light emitting diodes ("LEDs"). LED cable 146 and camera cable 148 pass through the third drive tube lumen 126 and the camera mounting collar apertures 128, and are then wrapped about a shank portion of the mounting collar 46, in order to provide strain relief protection for the connections of those cables to the respective LED 140 and camera 50.

Figure 12:
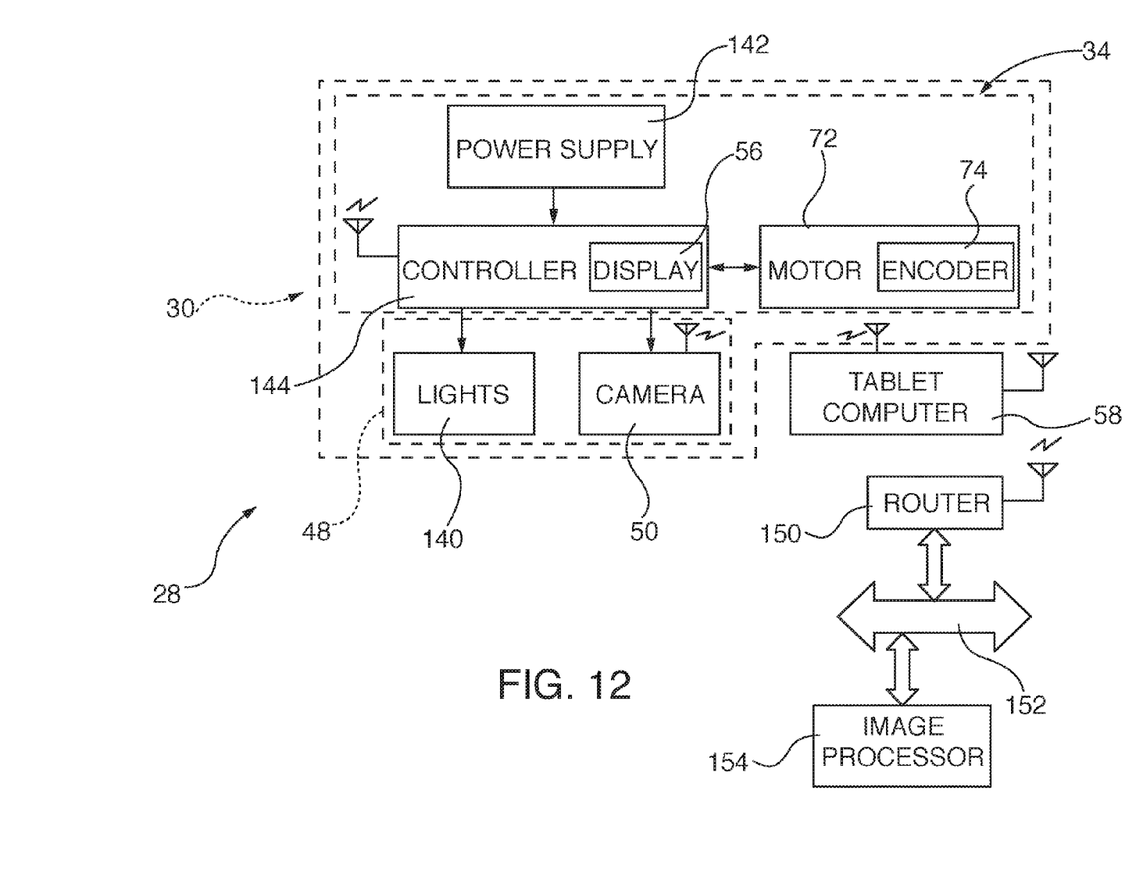
FIG. 12 is block diagram of the electrical circuits incorporated into the inspection scope of FIG. 1.

The block diagram of FIG. 12 shows interoperable connection of components and subsystems within the inspection system 28. Electro-mechanical structures of the inspection scope 30, the control box 34, and the camera housing 48 are shown schematically in dashed lines. Power supply 142, shown here for illustrative purposes within the control box 34, provides power for the controller 144, the display 56, the motor 72 and its encoder 74, the lighting system 140 and the camera 50. The controller 144 controls the lighting 140, camera 50, motor 72 and in some embodiments receive encoder data from the encoder 74. In some embodiments, the controller 144 has wireless communication capability for direct or indirect communication via a known wireless router 150 or via any known form of data communications network, including the Internet. In some embodiments, the controller 144 and/or the camera 50 are in wireless or hard-wired communication with the tablet computer 58 or an image processor 154 or any other type of known workstation.

Referring to FIGS. 1, 3, and 12, the inspection system 28 is used to inspect internal structure of a power generation machine 20, such as a gas turbine engine, by affixing the inspection scope 30 mounting flange 38 to an inspection port 22 or other machine inspection entry site, while inserting the inspection scope telescoping portion 32, including the camera housing 48 into the machine's interior. Once the inspection scope 30 is positioned for inspection, the camera housing 48 is advanced into the machine by rotating the driven gear 64 and its attached drive hub 76 with a hand crank 69 that is coupled to the controller box 34, or by operating the self-contained internal motor 72, thereby rotating the first drive tube 86, and advancing the second 112 and/or third 122 drive tube and ultimately the camera housing 48, with its spherical, 360 degree camera 50 within the power generation machine, along the inspection scope extension axis T, without rotating the camera 50 about the extension axis T. The 360-degree images generated within the camera field of view are captured in one or more positions along the extension axis T.

In many inspection embodiments, camera 50 images are captured at plural positions along the extension axis T. In embodiments where the inspection scope 30 is provided with a position encoder, such as the position encoder 74 of the motor 72, the encoder generates position output data that is correlated with axial displacement of the camera 50 field of view along the extension axis T. An image processing system in the controller 144, remote tablet or other computer 58 or in a remote, dedicated image processing workstation 154 determines axial displacement position of the camera field of view with the position encoder 74 output data, and correlates the determined axial displacement position T with a corresponding position within the corresponding camera image. Correlation of encoder 74 output position data with an image is performed with known, commercially available data acquisition hardware, and software. In some embodiments, the controller 144, and/or remote computers, such as the tablet computer 58, and/or the image processing system 154 archive images and/or encoder position data. In some embodiments, real-time and/or archived images are also viewable on the display 56 of the controller box 34. In some embodiments, the controller 144 automatically controls advancement of the camera housing 48 along the extension axis T by controlling the motor 72 in a feedback loop with the encoder 74.

In some embodiments, the image processing system, wherever located, combines plural inspection images into a navigable composite image, which is analogous to "street view" geographic mapping that is available in some Web-based applications. Commercially available image combining, and image-navigation software packages, operable on controller and/or computer hardware platforms, include the krpano Panorama Viewer, which is available from krpano Gesellschaft mbH of Deutschkreutz, Austria.

While reference to an exemplary controller 144 or tablet computer 58, or remote workstation 154 platform architecture, and implementation of operational tasks by software modules executed by the respective device's internal processor, it is also to be understood that exemplary embodiments of the invention are implemented in various forms of hardware, software, firmware, special purpose processors, or a combination thereof. Preferably, aspects of the invention embodiments are implemented in software as a program tangibly embodied on a non-volatile, non-transitory signal, program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. In addition, various other peripheral devices may be connected to the computer/controller platform.

It is to be understood that, because some of the constituent system components and method steps depicted in the accompanying figures are preferably implemented in software, the actual connections between the system components (or the process steps) may differ depending upon the manner in which the exemplary embodiments are programmed. Specifically, any of the computer platforms or devices may be interconnected using any existing or later-discovered networking technology; they may all be connected through a lager network system, such as a corporate network, metropolitan network or a global network, such as the Internet.

Although various embodiments that incorporate the invention have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted", "connected", "supported", and "coupled", and variations thereof are used broadly and encompass direct and indirect mountings, connections, supports, and couplings. Further, "connected" and "coupled" are not restricted to physical, mechanical, or electrical connections or couplings.

What is claimed is:

1. A system for internal inspection of a power generation machine, comprising:
    a single-axis, extendable inspection scope, for insertion into an inspection port of a power generation machine, having:
        first, and second nested, telescoping tubes, respectively having proximal and distal ends and axial length,
            the second telescoping tube having an axial groove on an outer circumferential surface thereof,
            the first telescoping tube having a first anti-rotation collar coupled proximal the distal end thereof, in sliding engagement with the axial groove of the second telescoping tube;
        first and second nested drive tubes retained within the telescoping tubes, respectively having proximal and distal ends and axial length,
            the first drive tube having a first drive bushing coupled to the distal end thereof, both of which are rotatable within the telescoping tubes, the first drive bushing defining a bore with female drive threads,
            the second drive tube defining external male drive threads in engagement with the first drive bushing female threads;
        a camera-mounting collar rigidly coupled to the respective distal ends of the second telescoping tube and the second drive tube, preventing relative rotation thereof;
        a rotatable drive hub coupled to the proximal end of the first drive tube, for selective rotation thereof;
        a mounting flange coupled to the first telescoping tube, for affixation to a power generation machine inspection port; and
    a spherical camera, having a 360 degree field of view, coupled to the camera mounting collar, for insertion into a power generation machine and capture of inspection images therein.

2. The system of claim 1, further comprising:
    a distal portion of the rotatable drive hub oriented within the proximal end of the first telescoping tube, and engaged within the first drive tube;
    a proximal portion of the drive hub coupled to a driven gear that is external the first telescoping tube;
    a first drive gear engaged with the driven gear, for rotating the driven gear and the drive hub; and
    a drive apparatus coupled to the first drive gear.

3. The system of claim 2, the drive apparatus comprising a hand crank.

4. The system of claim 2, the drive apparatus comprising an electric motor.

5. The system of claim 2, further comprising:
    the first drive gear directly engaged with the driven gear, driven by a hand crank drive apparatus; and
    a second drive gear directly engaged with the driven gear, driven by an electric motor;
    the respective drive gears independently and selectively capable of driving the driven gear.

6. The system of claim 1, the first anti-rotation collar retaining a ball bearing that is in engagement within the axial groove of the second telescoping tube.

7. The system of claim 1, further comprising at least one additional telescoping tube interposed and nested between the first and second telescoping tubes, each additional telescoping tube defining an axial groove on an outer circumferential surface thereof, for engagement with an anti-rotation collar of a circumscribing telescoping tube, and an anti-rotation collar coupled proximal a distal end thereof, in sliding engagement with the axial groove of an inscribed telescoping tube retained therein.

8. The system of claim 1, further comprising at least one additional drive tube interposed and nested between the first and second drive tubes, each additional drive tube defining male drive threads on an outer circumferential surface thereof, for engagement with female threads of a drive bushing of a circumscribing drive tube, and a drive bushing coupled proximal a distal end thereof, in engagement with drive threads of an inscribed drive tube retained therein.

9. The system of claim 1, further comprising a camera housing coupled to the camera collar, enveloping the camera.

10. The system of claim 9, the camera housing further comprising an illumination system, coupled thereto, for illuminating the camera field of view.

11. The system of claim 1, further comprising:
    a position encoder, for correlating hub rotation with axial displacement of the camera field of view; and
    an image processing system coupled to the camera and the position encoder, for storing plural images taken at different camera axial displacement positions, and for combining plural inspection images into a composite image.

12. A system for internal inspection of a power generation machine, comprising:
    a single-axis, extendable inspection scope, which defines an extension axis, for insertion into an inspection port of a power generation machine, the scope having:
        first, second, third, and fourth nested, telescoping tubes, respectively having proximal and distal ends and axial length,
            the second, third and fourth telescoping tubes respectively having an axial groove on an outer circumferential surface thereof,
            the first telescoping tube having a first anti-rotation collar coupled proximal the distal end thereof, in sliding engagement with the axial groove of the second telescoping tube,
            the second telescoping tube having a second anti-rotation collar coupled proximal the distal end thereof, in sliding engagement with the axial groove of the third telescoping tube, the third telescoping tube having a third anti-rotation collar coupled proximal the distal end thereof, in sliding engagement with the axial groove of the fourth telescoping tube;

first, second and third nested drive tubes retained within the telescoping tubes, respectively having proximal and distal ends and axial length, the first drive tube having a first drive bushing coupled to the distal end thereof, both of which are rotatable within the fourth telescoping tube, the first drive bushing defining a bore with female drive threads, the second drive tube defining external male threads in engagement with the first drive bushing female threads, and having a second drive bushing coupled to the distal end thereof, both of which are rotatable within the fourth telescoping tube, the second drive bushing defining a bore with female drive threads, the third drive tube defining external male threads in engagement with the second drive bushing female threads;

a camera-mounting collar rigidly coupled to the respective distal ends of the fourth telescoping tube and the third drive tube, preventing relative rotation thereof;

a rotatable drive hub coupled to the proximal end of the first drive tube, for selective rotation thereof;

a mounting flange coupled to the first telescoping tube, for affixation to a power generation machine inspection port; and a spherical camera, having a 360 degree field of view, coupled to the camera mounting collar, for insertion into a power generation machine and capture of inspection images therein.

13. The system of claim 12, at least one of the anti-rotation collars retaining a ball bearing that is in engagement within the axial groove of the second telescoping tube.

14. The system of claim 12, further comprising:
a distal portion of the rotatable drive hub oriented within the proximal end of the first telescoping tube, and engaged within the first drive tube;
a proximal portion of the drive hub coupled to a driven gear that is external the first telescoping tube;
a first drive gear engaged with the driven gear, for rotating the driven gear and the drive hub; and
a drive apparatus coupled to the first drive gear.

15. The system of claim 14, further comprising:
a controller box retaining the driven gear and the first drive gear, the first drive gear directly engaged with the driven gear, driven by a hand crank drive apparatus; and
a second drive gear directly engaged with the driven gear, driven by an electric motor, both of which are retained within the drive gear housing;
the respective drive gears independently and selectively capable of driving the driven gear; and
a visual display incorporated within the controller box, for viewing images captured within the camera field of view.

16. The system of claim 12, further comprising a camera housing coupled to the camera collar, enveloping the camera; and an illumination system, coupled to the camera housing, for illuminating the camera field of view.

17. The system of claim 12, further comprising:
a position encoder, for correlating hub rotation with axial displacement of the camera field of view; and an image processing system coupled to the camera and the position encoder, for storing plural images taken at different camera axial displacement positions, and for combining plural inspection images into a navigable composite image.

18. A method for internal inspection of a power generation machine, comprising:
providing a system for inspection of a power generation machine, the system including:
a single-axis, extendable inspection scope, which defines an extension axis, for insertion into an inspection port of a power generation machine, the scope having:
first, and second nested, telescoping tubes, respectively having proximal and distal ends and axial length,
the second telescoping tube having an axial groove on an outer circumferential surface thereof,
the first telescoping tube having a first anti-rotation collar coupled proximal the distal end thereof, in sliding engagement with the axial groove of the second telescoping tube;
first and second nested drive tubes retained within the telescoping tubes, respectively having proximal and distal ends and axial length,
the first drive tube having a first drive bushing coupled to the distal end thereof, both of which are rotatable within the telescoping tubes, the first drive bushing defining a bore with female drive threads,
the second drive tube defining external male drive threads in engagement with the first drive bushing female threads;
a camera-mounting collar rigidly coupled to the respective distal ends of the second telescoping tube and the second drive tube, preventing relative rotation thereof;
a rotatable drive hub coupled to the proximal end of the first drive tube, for selective rotation thereof;
a mounting flange coupled to the first telescoping tube, for affixation to a power generation machine inspection port; and
a spherical camera, having a 360 degree field of view, coupled to the camera mounting collar, for insertion into a power generation machine and capture of inspection images therein;
affixing the mounting flange to an inspection port, or other machine-inspection entry site in a power generation machine, while inserting the inspection scope therein;
rotating the drive hub, thereby rotating the first drive tube, and advancing the second drive tube and the camera field of view within the power generation machine, without rotating the camera about the inspection scope extension axis; and
capturing respective camera images within the power generation machine at plural positions, as the camera field of view is advanced within the machine.

19. The method of claim 18, further comprising:
the provided system for inspection further including a position encoder, for correlating hub rotation with axial displacement of the camera field of view, the position encoder generating position output data, and an image processing system coupled to the camera and the position encoder, for storing plural images taken at different camera axial displacement positions, and for combining plural inspection images into a composite image;

the image processing system determining axial displacement position of the camera field of view with the position encoder output data, correlating the determined axial displacement position with a corresponding position within the camera image; and the image processing system combining plural inspection images into a navigable composite image.

20. The method of claim 19, further comprising providing a motorized drive coupled to the rotatable hub, for rotating the hub and automatically advancing the camera field of view within the power generation machine.

* * * * *